United States Patent
Dawson

(10) Patent No.: US 6,455,552 B1
(45) Date of Patent: Sep. 24, 2002

(54) COMBINATION OF A GABA$_A$ α5 INVERSE AGONIST AND A MUSCARINIC AGONIST

(75) Inventor: Gerard Raphael Dawson, Saffron Walden (GB)

(73) Assignee: Merck Sharp & Dohme Ltd., Hoddesdon (*) Notice: Subject to any disclaimer, the term of this patent is extended or adjusted under 35 U.S.C. 154(b) by 0 days.

(21) Appl. No.: 09/622,952

(22) PCT Filed: Mar. 16, 1999

(86) PCT No.: PCT/GB99/00801

§ 371 (c)(1),
(2), (4) Date: Aug. 24, 2000

(87) PCT Pub. No.: WO99/47171

PCT Pub. Date: Sep. 23, 1999

(30) Foreign Application Priority Data

Mar. 16, 1998 (GB) .............................................. 9805557

(51) Int. Cl.$^7$ ........................ A61K 31/44; A61K 31/502
(52) U.S. Cl. ........................................ 514/356; 514/248
(58) Field of Search ................................... 514/248, 356

(56) References Cited

U.S. PATENT DOCUMENTS

4,647,580 A   3/1987  Rozkowski .................. 514/464

FOREIGN PATENT DOCUMENTS

| WO | WO 92/03433 | 3/1992 |
| WO | WO 96/25948 | 8/1996 |
| WO | WO 98/04560 | 2/1998 |
| WO | WO 98/50385 | 11/1998 |

OTHER PUBLICATIONS

Soncrant et al., Psychopharmacology, 112, p. 421 (1993).*
Folstein, et al., J. Psychiat. Res., 12:189–198 (1975).
Tombaugh, et al., Jags, 40:922–935 (1992).

* cited by examiner

*Primary Examiner*—Phyllis G. Spivack
(74) *Attorney, Agent, or Firm*—J. Eric Thies; Shu Muk Lee; Melvin Winokur

(57) ABSTRACT

A combination of a muscarinic agonist and an inverse agonist of the GABA$_A$ α5 receptor subtype useful in treating neurodegenerative conditions such as Alzheimer's Disease is disclosed.

6 Claims, No Drawings

COMBINATION OF A GABA$_A$ α5 INVERSE AGONIST AND A MUSCARINIC AGONIST

This is an application under 35 U.S.C. 371 of PCT/GB99/00801 and claims priority from Great Britain Application No. 9805557.7, filed Mar. 16, 1998.

The present invention relates to a combination of an muscarinic agonist and an inverse agonist of the GABA$_A$ α$_5$ receptor subtype, and the use of the combination in treating neurodegenerative conditions such as Alzheimer's Disease.

Alzheimer's Disease is a poorly understood neurodegenerative condition mainly affecting the elderly but also younger people who are generally genetically predispositioned to it.

One postulated method of treatment comprises the administration of muscarinic agonists which act on the cholinergic system. However this method suffers from the disadvantages that these compounds induce a range of side-effects including diarrhoea, salivation and nausea.

The present invention provides a new and surprisingly effective synergistic combination of an muscarinic agonist and an inverse agonist of the GABA$_A$ α$_5$ receptor subtype for separate, sequential or simultaneous administration.

The present invention provides a greater than expected improvement in the condition of subjects suffering from a neurodegenerative with an associated cognitive deficit, such as Alzheimer's Disease or Parkinson's disease, or from a cognitive deficit which may arise from a normal process such as aging or from an abnormal process such as injury, than would be expected from administration of the active ingredients alone. Further, the combination allows for a lower overall dose of each of the active ingredients to be administered thus reducing side effects and decreasing any reduction in the effectiveness of each of the active ingredients over time.

Muscarinic agonists which may be used include any which are known to the skilled person. Examples are methacholine and its chloride, carbachol, bethanechol, arecholine, pilocarpine, muscarine, McN-A-343, oxotremorine, milameline, xanomeline, cis-methyldioxalane, pirenzepine, gallamine, SB 202026, AF102B, AFDX 116 and RS-86.

Any inverse agonist of the GABA$_A$ α$_5$ receptor subtype may be used which fulfills the criteria of WO-A-9625948. The inverse agonist may be either binding selective for the α$_5$ subtype or functionally selective, or both. Thus the inverse agonist is preferably an antagonist, or has insignificant agonist or inverse agonist properties at the other GABA$_A$ α receptor subtypes when measured in oocytes as described in WO-A-9625948.

Thus the inverse agonist preferably has a functional efficacy at the α$_5$ receptor subunit of less than −20% and functional efficacies at the α$_1$, α$_2$, and α$_3$ receptor subunits of between −20 and +20%. By functional efficacy is meant the percentage modulation of the EC$_{20}$ response produced by GABA, upon coadministration of the inverse agonist, in oocytes expressing GABA$_A$ receptor channels containing the α receptor subunit under test. Details of this measurement are given in WO-A-9625948.

The inverse agonist preferably binds selectively to GABA$_A$ receptors containing the α$_5$ subunit 10, 25 and particularly 50 times compared to GABA$_A$ receptors subunits containing the α$_1$, α$_2$ or α$_3$ subunits. Preferably this binding selectivity is shown over all these subunits.

A preferred class of inverse agonists, which are disclosed in WO-A-9850385, are of formula I:

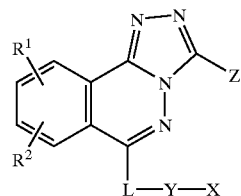

wherein:
R$^1$ is hydrogen, halogen or CN or a group C$_{1-4}$alkyl, C$_{2-4}$alkenyl, C$_{2-4}$alkynyl, C$_{1-4}$alkoxy, C$_{2-4}$alkenyloxy or C$_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or CF$_3$ groups;

R$^2$ is hydrogen, halogen or CN or a group C$_{1-4}$alkyl, C$_{2-4}$alkenyl, C$_{2-4}$alkynyl, C$_{1-4}$alkoxy, C$_{2-4}$alkenyloxy or C$_{2-4}$alkynyloxy each of which groups is unsubstituted or substituted with one or two halogen atoms;

L is O, S or NR$''$, where R$''$ is H, C$_{1-6}$alkyl or C$_{3-6}$cycloalkyl;

X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene ring and the heteroaromatic ring being optionally substituted by R$^x$ and/or R$^y$ and/or R$^z$, where R$^x$ is halogen, R$^3$, OR$^3$, OCOR$^3$, NR$^4$R$^5$, NR$^4$COR$^5$, tri(C$_{1-6}$alkyl)silylC$_{1-6}$alkoxyC$_{1-4}$alkyl, CN or R$^9$, R$^y$ is halogen, R$^3$, OR$^3$, OCOR$^3$, NR$^4$R$^5$, NR$^4$COR$^5$ or CN and R$^z$ is R$^3$, OR$^3$ or OCOR$^3$, where R$^3$ is C$_{1-6}$alkyl, C$_{2-6}$alkenyl, C$_{2-6}$alkynyl, C$_{3-6}$cycloalkyl, hydroxyC$_{1-6}$alkyl and R$^3$ is optionally mono, di- or tri-fluorinated, R$^4$ and R$^5$ are each independently hydrogen, C$_{1-6}$alkyl, C$_{2-6}$alkenyl, C$_{2-6}$alkynyl, C$_{3-6}$cycloalkyl or CF$_3$ or R$^4$ and R$^5$, together with the nitrogen atom to which they are attached, form a 4–7 membered heteroaliphatic ring containing the nitrogen atom as the sole heteroatom, and R$^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and R$^9$ is optionally substituted by one, two or three substituents independently chosen from halogen atoms and C$_{1-4}$alkyl, C$_{2-4}$alkenyl, C$_{2-4}$alkynyl, C$_{1-4}$alkoxy, C$_{2-4}$alkenyloxy and C$_{2-4}$alkynyloxy groups each of which groups is unsubstituted or substituted by one, two or three halogen atoms, and when X is a pyridine derivative, the pyridine derivative is optionally in the form of the N-oxide and providing that when X is a tetrazole derivative it is protected by a C$_{1-4}$alkyl group; or X is phenyl optionally substituted by one, two or three groups independently selected from halogen, cyano, C$_{1-6}$alkyl, C$_{2-6}$alkenyl, C$_{2-6}$alkynyl and C$_{3-6}$cycloalkyl;

Y is optionally branched C$_{1-4}$alkylidene optionally substituted by an oxo group or Y is a group (CH$_2$)$_j$O wherein the oxygen atom is nearest the group X and j is 2, 3 or 4;

Z is a 5-membered heteroaromatic ring containing 1, 2 or 3 heteroatoms independently selected from oxygen, nitrogen and sulphur, at most one of the heteroatoms being oxygen or sulphur and providing that when two of the heteroatoms are nitrogen an oxygen or sulphur atom is also present and that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$ or $R^7$ and $R^8$, together with the nitrogen atom to which they are attached, form a 4–7 membered heteroaliphatic ring containing the nitrogen atom as the sole heteroatom;

or a pharmaceutically acceptable salt thereof.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-4}$alkyl", "$C_{2-4}$alkenyl", "$C_{2-6}$alkenyl", "hydroxy$C_{1-6}$alkyl", "$C_{2-4}$alkyl" and "$C_{2-6}$alkynyl" are to be construed in an analogous manner.

The expression "$C_{3-6}$cycloalkyl" as used herein includes cyclic propyl, butyl, pentyl and hexyl groups such as cyclopropyl and cyclohexyl.

Suitable 5- and 6-membered heteroaromatic rings include pyridinyl, pyridazinyl, pyrimidinyl, pyrazinyl, pyrrolyl, pyrazolyl, oxazolyl, isoxazolyl, thiazolyl, isothiazolyl, imidazolyl, oxadiazolyl and thiadiazolyl groups. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine.

The term "halogen" as used herein includes fluorine, chlorine, bromine and iodine, of which fluorine and chlorine are preferred.

As used herein the term "$C_{1-6}$alkoxy" includes methoxy and ethoxy groups, and straight-chained, branched and cyclic propoxy, butoxy, pentoxy and hexoxy groups, including cyclopropylmethoxy. Derived expressions such as "$C_{2-6}$alkenyloxy", "$C_{2-6}$alkynyloxy", "$C_{1-4}$alkoxy", "$C_{2-4}$alkenyloxy" and "$C_{2-4}$alkyloxy" should be construed in an analogous manner.

Four particular compounds which can be used are:

6-(1-methylimidazol-4-yl)methyloxy-3-(5-methylisoxazol-3-yl)-1,2,4-triazolo[3,4-a]phthalazine;

3-(5-methylisoxazol-3-yl)-6-(1-methyl-1,2,3-triazol-4-yl) methyloxy-1,2,4-triazolo[3,4-a]phthalazine;

3-(5-methylisoxazol-3-yl)-6-(2-pyridyl)-1,2,4-triazolo[3,4-a]phthalazine; and 3-(5-methylisoxazol-3-yl)-6-(1-methylimidazol-4-yl)- 1,2, 4-triazol-3-ylmethyloxy-1,2,4-triazolo[3,4-a]phthalazine.

The second of the above compounds is particularly favoured.

The present invention also provides a pharmaceutical composition comprising an muscarinic agonist, an inverse agonist of the $GABA_A$ $\alpha_5$ receptor subtype and a pharmaceutically acceptable carrier.

There is also provided a kit of parts comprising a first pharmaceutical composition comprising an muscarinic agonist and a first pharmaceutically acceptable carrier and a second pharmaceutical composition comprising an inverse agonist of the $GABA_A$ $\alpha_5$ receptor subtype and a second pharmaceutically acceptable carrier for simultaneous, sequential or separate administration.

There is further provided a combination of an muscarinic agonist and an inverse agonist of the $GABA_A$ $\alpha_5$ receptor subtype for use in a method of treatment of the human body, particularly for the treatment of a neurodegenerative disorder with associated cognitive deficit such as Alzheimer's Disease or Parkinson's disease, or of a cognitive deficit arising from a normal process such as aging or of an abnormal process such as injury. The combination is particularly beneficial in the treatment of Alzheimer's Disease.

There is also provided the use of a combination of an muscarinic agonist and an inverse agonist of the $GABA_A$ $\alpha_5$ receptor subtype in the manufacture of a medicament for the treatment of a neurodegenerative disorder such as Alzheimer's Disease or Parkinson's disease, or of a cognitive deficit arising from a normal process such as aging or of an abnormal process such as injury. The treatment of Alzheimer's Disease is particularly preferred.

There is also disclosed a method of treatment of a subject suffering from a neurodegenerative disorder, such as Alzheimer's Disease or Parkinson's disease, or a cognitive deficit arising from a normal process such as aging or an abnormal process such as injury, which comprises administering to that subject a therapeutically effective amount of a combination of an muscarinic agonist and an inverse agonist of the $GABA_A$ $\alpha_5$ receptor subtype. The treatment of Alzheimer's Disease is particularly preferred.

The pharmaceutical compositions of the present invention are preferably in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of each active ingredient of the present invention. Typical unit dosage forms contain from 1 to 100 mg, for example 1, 2, 5, 10, 25, 50 or 100 mg, of each active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

For the treatment of a neurodegenerative condition, a suitable dosage level is about 0.01 to 250 mg/kg per day, preferably about 0.01 to 100 mg/kg per day, and especially about 0.01 to 5 mg/kg of body weight per day of each active ingredient. The compounds may be administered on a regimen of 1 to 4 times per day. In some cases, however, dosage outside these limits may be used.

The synergistic effect of the combination of the present invention can be shown, for example, by comparing the combined dosage of the combination with dosages of the same amount of each of the active ingredients separately on subjects using the Mini-Mental State Examination (MMSE) as described in Folstein and Folstein J. Psychiat. Res., 1975, 12, 189–198 or a variant thereof as discussed in Tombaugh and McIntyre, JAGS, 1992, 40, 922–935.

What is claimed is:

1. A combination of the muscarinic agonist arecholine and the inverse agonist 3-(5-methylisoxazol-3-yl)-6-(1-methyl-1,2,3-triazol-4-yl)methyloxy-1,2,4-triazolo[3,4-a]phthalazine of the $GABA_A$ $\alpha 5$ receptor subtype for separate, sequential or simultaneous administration.

2. A combination according to claim 1 wherein the inverse agonist has a functional efficacy at the $\alpha_5$ receptor subtype of less than 20%, and a functional efficacy at the $\alpha_1$, $\alpha_2$ and $\alpha_3$ receptor subtypes of between −20 and +20%.

3. A combination according to claim 1 wherein the inverse agonist has a binding ration of greater than 10:1 to $GABA_A$ receptors containing the $\alpha_5$ receptor subtype compared to $GABA_A$ receptors containing the $\alpha_1$, $\alpha_2$ or $\alpha_3$ subtypes.

4. A pharmaceutical composition comprising a combination as defined if claim 1 and a pharmaceutically acceptable carrier for simultaneous administration.

5. A kit of parts comprising a first pharmaceutical composition comprising arecholine and a first pharmaceutically acceptable carrier and a second pharmaceutical composition comprising 3-(5-methylisoxazol-3-yl)-6-(1-methyl-1,2,3-triazol-4-yl)methyloxy-1,2,4-triazolo[3,4-a]phthalazine and a second pharmaceutically acceptable carrier for simultaneous, separate or sequential administration.

6. A method for the treatment of a subject suffering from a neurodegenerative disorder or a cognitive deficit comprising administering to that subject a therapeutically effective amount of a combination of arecholine and 3-(5-methylisoxazol-3-yl)-6-(1-methyl-1,2,3-triazol-4-yl)methyloxy-1,2,4-triazolo[3,4-a]phthalazine.

* * * * *